(12) United States Patent
Mäkinen

(10) Patent No.: US 8,457,730 B2
(45) Date of Patent: Jun. 4, 2013

(54) TECHNIQUES FOR DETERMINING HEARING THRESHOLD

(75) Inventor: Ville Mäkinen, Espoo (FI)

(73) Assignee: Senseg Oy, Espoo (FI)

( * ) Notice: Subject to any disclaimer, the term of this patent is extended or adjusted under 35 U.S.C. 154(b) by 741 days.

(21) Appl. No.: 12/516,729

(22) PCT Filed: Nov. 8, 2007

(86) PCT No.: PCT/FI2007/050597
§ 371 (c)(1),
(2), (4) Date: May 28, 2009

(87) PCT Pub. No.: WO2008/065239
PCT Pub. Date: Jun. 5, 2008

(65) Prior Publication Data
US 2009/0326405 A1 Dec. 31, 2009

(30) Foreign Application Priority Data
Nov. 29, 2006 (FI) .................................... 20065759

(51) Int. Cl.
*A61B 5/04* (2006.01)

(52) U.S. Cl.
USPC ........................................................ 600/544

(58) Field of Classification Search
USPC ................................................ 600/544, 545
See application file for complete search history.

(56) References Cited

U.S. PATENT DOCUMENTS

| | | | |
|---|---|---|---|
| 4,038,496 A * | 7/1977 | Feezor | 73/585 |
| 4,419,544 A * | 12/1983 | Adelman | 381/94.3 |
| 4,913,160 A | 4/1990 | John | |
| 4,974,602 A | 12/1990 | Abraham-Fuchs et al. | |
| 5,230,344 A | 7/1993 | Ozdamar et al. | |
| 6,343,230 B1 | 1/2002 | Smits et al. | |
| 2005/0018858 A1 * | 1/2005 | John | 381/60 |

OTHER PUBLICATIONS

Auditory Event-Related Responses are Generated Independently of Ongoing Brain Activity. Makinen et al., NeuroImage 24 (2005) 961-968.*
Tiitinen et al. (Averaged and single-trial brain responses in the assessment of human sound detection). Auditory and Vestibular Systems. vol. 16. No. 6. Apr. 25, 2005.*
Maikinen et al., Transient Brain Responses Predict the Temporal Dynamics of Sound Detection in Humans, NeuroImage, vol. 21, No. 2, Feb. 2004, pp. 701-706, XP002581421.

(Continued)

Primary Examiner — Patricia Mallari
Assistant Examiner — Christian Jang
(74) *Attorney, Agent, or Firm* — Schwegman Lundberg & Woessner, P.A.

(57) ABSTRACT

A computerized method for determining a test subject's (TS) hearing threshold (HT). An acoustic stimulus (AS, 102) is applied the test subject's (TS) ear. The stimulus intensity is increased during a ramp, with a predetermined dependency on time, such that the intensity begins below the hearing threshold and ends above it. The test subject's brain response (104), which includes a transient brain response (TR)1 is non-invasively recorded during the ramp section. The stimulus-response cycle is repeated several times. The recorded brain responses and stored a-priori information on transient brain response to the acoustic stimulus are used to determine a combined time interval between the acoustic stimulus and the transient brain response. The test subject's hearing threshold is determined based on the predetermined dependency on time of the intensity during the ramp and the combined time interval between the acoustic stimulus and the transient brain response.

13 Claims, 2 Drawing Sheets

OTHER PUBLICATIONS

Açikgöz et al., "Audiometric Threshold Screening Method Using Envelope Detection Filters of Intensity Ramping Click Auditory Steady-State Responses", Proceedings of the 28th IEEE EMBS Annual International Conference, New York City, USA, Aug. 30-Sep. 3, 2006, pp. 4983-4986, ISSN 1557-170X. Pub. Date: Aug. 2006, Abstract; Section II.

Gevins, "Analysis of the Electromagnetic Signals of the Human Brain: Milestones, Obstacles, and Goals", IEEE Trans Biomed Eng., Dec. 1984, vol. Bme-31, No. 12, pp. 833-850, ISSN 0018-9294, Pub. Date: Dec. 1984, Abstract; Fig. 2, 8, 9; Subsection III C (1).

* cited by examiner

TECHNIQUES FOR DETERMINING HEARING THRESHOLD

PARENT CASE INFORMATION

This application is the National Phase of PCT/FI2007/050597 filed on Nov. 8, 2007, which claims priority under 35 U.S.C. 119(e) to U.S. Provisional Application No. 60/925,994 filed on Apr. 24, 2007 and under 35 U.S.C. 119(a) to Patent Application No. 20065759 filed in Finland on Nov. 29, 2006, all of which are hereby expressly incorporated by reference into the present application.

BACKGROUND OF THE INVENTION

The invention relates to methods, equipment and software products for non-invasively determining a hearing threshold of a test subject, by recording one or more brain responses to one or more acoustic stimuli. Non-restrictive examples of the brain responses include electroencephalography (EEG) responses and magnetoencephalography (MEG) responses, commonly referred to as "brainwaves". The invention can be used in diagnostic and non-diagnostic applications.

A general problem in techniques which involve recording brainwave responses to an acoustic stimulus is that the brain response to a single acoustic stimulus is difficult to isolate from a huge variety of simultaneous brainwaves, most of which are unrelated to the acoustic stimulus. Furthermore, the relationship between the measured brain activity and the hearing threshold is not straightforward. In addition the commonly employed auditory brain stem responses reflect auditory processing at a rather low level in the central nervous system and may not provide information on auditory processes going on at higher levels, such as the auditory cortex.

US patent application no 2005/0018858 (Michael Sasha John) discloses various techniques for screening, threshold and diagnostic for evaluation of a patient's hearing. The techniques disclosed by John include acoustically presenting a modulated noise stimulus at a specific intensity to the patient's ear; recording response data related to the patient's response to the stimulus; performing signal analysis on the response data to generate result data; and evaluating the result data using at least one statistical technique to determine the presence of at least one auditory steady-state response. John proposes using EEG data as the response data. He proposes on-off modulation of a stimulus which contains an increasing and/or decreasing ramp section. The on-off modulation of the ramping stimulus is essentially equivalent to subjecting the test subject to several consecutive stimuli, wherein the intensity of one stimulus is higher or lower than the previous stimulus. John also proposes isolating the relevant brain response from other simultaneous brainwaves (which John calls "EEG noise") by processing multiple stimulus-response cycles via complex statistical procedures.

A specific problem in the techniques disclosed by John is that the complex statistical procedures consume computational resources. Also, the technique proposed by John requires two nested levels of repetition, which also consumes time and computational resources. One level of repetition stems from the fact that even at a constant intensity, a stimulus-response cycle should be repeated and the time-aligned responses should be averaged to suppress the EEG noise. The other level of repetition is caused by the on-off modulation of the increasing and/or decreasing ramp. Such consumption of time is a burden on the test subject and test personnel. Prolonged testing may influence the test subjects' hearing and falsify the obtained results.

BRIEF DESCRIPTION OF THE INVENTION

An object of the invention is to develop non invasive techniques for determining the hearing threshold of a test subject such that one or more of the problems associated with the prior art techniques can be alleviated.

An aspect of the invention is a method according to claim 1, which comprises the following steps:

a) storing a-priori information on transient brain response to at least one acoustic stimulus;

b) applying an acoustic stimulus having multiple parameters (such as intensity, frequency, etc.) to at least one ear of the test subject, wherein the acoustic stimulus contains at least one ramp section in which at least one of the multiple parameters (typically at least intensity) of the acoustic stimulus are varied according to at least one ramping function, wherein the at least one ramping function has a predetermined dependency on time, such that in the beginning or end of the at least one ramp section the acoustic stimulus is below or above, respectively, of the test subject's hearing threshold;

c) non-invasively recording a brain response of the test subject within a predetermined time window in relation to the at least one ramp section, wherein the recorded brain response contains a transient brain response;

d) obtaining a plurality of recorded brain responses by repeating the two previous steps several times;

e) using the plurality of recorded brain responses and the stored a-priori information on transient brain response to the at least one acoustic stimulus to determine a combined time interval between the acoustic stimulus and the transient brain response;

f) determining the hearing threshold of the test subject based on the predetermined dependency on time of the at least one ramping function and the combined time interval between the acoustic stimulus and the transient brain response.

As regards step a), the stored a-priori information on transient brain response to the one acoustic stimulus is used to detect the transient brain response that is buried under other signal components which, from the point of view of determining hearing threshold, are essentially "EEG noise". In step b), one or more parameters of the acoustic stimulus, typically at least intensity, are varied such that the stimulus contains a rising ramp. In the context of the present invention, a rising ramp means a stimulus or section of the stimulus in which one or more parameters (typically at least intensity, but optionally frequency or harmonic composition) are varied such that the beginning of the ramp is inaudible to the test subject while its end is audible. In other words, the ramp begins under the test subject's expected hearing threshold and ends above it. Furthermore, the rise characteristics of the ramp are appropriately dimensioned, such that reasonably accurate measurements are possible. The following description is based on the assumption that the ramp rises linearly (in decibels per unit of time). A linear ramp provides a simple relation between timing and stimulus intensity, but the ramp linearity is not an essential feature of the invention. The rise characteristics are called the slope of the ramp. If the slope is too steep (the intensity increases by too many decibels per unit of time), any variation in timing-related measurements, such as latency, causes too much variation in the corresponding stimulus intensity. In this context, latency means a time delay which begins when the stimulus exceeds the hearing threshold and ends when the transient response is detectable. Also, the inherent inaccuracy of the human auditory system may cause problems in determining timing-related parameters, such as latency. On the other hand, making the stimulus slope too gentle broadens the time window in which the transient response is to be detected. Furthermore the duration and shape of the stimuli need to be appropriate. The transient response associated with the stimulus exceeding hearing threshold must be separable from other transient responses produced by other stimulus properties, such as the off-set response produced by ending of the stimulus. The inventors have discovered that the rise time of the acoustic stimulus, ie, the duration of the ramp from certainly below hearing threshold to certainly above hearing threshold, should be more than 10 ms and, preferably above 100 ms. On the other hand ramp durations above 5 second consume excessive time and introduce problems into the detection of the transient response. Thus a lower limit for the ramp duration is about 10 ms, preferably about 200 ms and optimally about 400 ms. An upper limit for the ramp duration is about 10 s, preferably about 2 s and optimally about 1 s. During the ramp, the stimulus intensity should increase from a value which is certainly below hearing threshold to a value which is certainly above hearing threshold but not inconvenient or harmfully loud. For example, the starting value can be between −10 and 10 dB, while the ending value can be between 50 and 90 dB.

In step c), the test subject's brain response to the stimulus is recorded by a non-invasive technique, such as EEG or MEG. The recording should span a time window in which the transient brain response is to be expected, which in practice means the duration of the ramp plus the latency delay and duration of the transient brain response. The idea is to enhance the likelihood of the brain response being caused by the ramp section of the acoustic stimulus. For example, the time window can span the duration of the ramp plus approximately 200 ms for normal adults and 400 ms for infants and certain groups of special test subjects.

The steps of applying the stimulus and recording the response are repeated several times in order to obtain a plurality of recorded brain responses.

Step e) comprises using the plurality of recorded brain responses and the a-priori information on transient brain response to the acoustic stimulus to determine a combined time interval between the acoustic stimulus and the transient brain response. Use of the a-priori information, such as known representative wave shapes of the P1 and N1 brain waves, improves detection of transient brain responses which may otherwise be buried under EEG noise. The combined time interval means a time interval value which is representative of the plurality of recorded brain responses. By way of a non-restrictive example, such a representative value may be obtained by time-aligning the recorded brain responses in relation to the acoustic stimulus. The time-aligned responses are then combined in a combinatory process which emphasizes a relative proportion of the transient response. Simple implementations of such a combinatory process include summing, averaging and multiplication. In more complex implementations of the combinatory process, the times of the brain response, relative to the stimulus, are only starting values, and the times of individual brain responses may be fine-tuned within some predetermined margin around the starting values, such that maximum correlation between the recorded brain responses is reached in a time window in which the transient brain response is expected. The representative value of the time interval between the acoustic stimulus and the transient brain response may be expressed as a single scalar value or as a distribution of values, for example.

The inventors have discovered that the human auditory system has some inherent inaccuracy with ramped stimuli, namely the fact that the transient activity is not accurately time-aligned to the stimulus. Thus conventional time-aligning techniques may not function or do so poorly. This is because the transient responses have both negative and positive deflections that cancel each other out in the averaging process, if the responses are not accurately time aligned. The following preferred embodiments of the inventive technique aim at alleviating this time-alignment problem.

A transformation capable of retaining temporal information of the possible transient response may be applied to each response signal measured during a single acoustic stimulus. The signals thus transformed are combined into an ensemble in a manner that retains the temporal information of the single-trial transient responses. A similar effect may be achieved by combining non-transformed signals in a non-linear fashion. Then the combined time interval of the transient response is determined from this ensemble.

A non-restrictive example of the above technique comprises band-pass filtering of single trials and then determining the combined time interval of the transient response, for example, as a single maximum or a few maxima between the onset and offset time of the stimulus. Then the latencies of the maxima are collected and a histogram of these is produced, and the combined time interval is determined from the histogram. This can be done, for example, by convoluting the histogram with a Gaussian wave of appropriate half width. The combined time interval is then the time point of the maximum of the convolution between the histogram and the wave shape.

A benefit of the invention is improved ability to detect transient brain responses to ramp stimuli even when conventional techniques for time-aligning trials fail to provide useful responses. These signals may be examined with special single-trial techniques, and the detected responses are used in determining hearing threshold.

A variant of the technique comprises detecting and estimating the sustained activity that follows the transient response for determining the time point when the sound exceeded the hearing threshold; with appropriate stimuli the sustained activity may track the intensity slope of the stimulus and the combined time interval could be obtained by estimating a predetermined time point (e.g. beginning) of a sustained response.

In step f), the test subject's hearing threshold is determined based on the predetermined dependency on time of the ramping function and the combined time interval between the acoustic stimulus and the transient brain response. In a simple example, in which the ramp increases from $V_0$ dB with a constant slope of k dB/s, a combined time interval of t seconds means a hearing threshold of approximately $V_0 + k*t$ dB.

A more accurate value for the hearing threshold may be determined by calculating the intensity of the acoustic stimulus at the time when the transient response occurred minus an experimentally-determined latency. The inventors have discovered that an appropriate latency value for the N1 response lies between 50 and 350 ms, a preferred range being 75 to 250 ms.

Another aspect of the invention is an apparatus for carrying out the above method. Yet another aspect of the invention is a software product for a computer-controlled testing apparatus, wherein execution of the inventive software product in the computer-controlled testing apparatus causes it to execute the method according to claim 1.

For cases in which the ramp intensity does not increase linearly, the general formula for determining the hearing threshold is as follows. Let V=f(t), wherein V denotes stimulus intensity, t denotes time and f denotes the ramping function by which the stimulus intensity is increased during the ramp. The hearing threshold of the test subject equals $V_{TS}$=f$(T_{TR}-T_{COR})$, wherein $T_{TR}$ denotes the point of time at which the transient response is detectable and $T_{COR}$ includes any time-related correction elements, most importantly the above-described latency.

Applying short ramps to hearing threshold determination requires accurate determination of the combined time interval between the acoustic stimulus and the transient brain responses. This is because in a short ramp stimulus, the sound pressure level increases steeply, and any inaccuracies in timing of the transient brain response cause large errors in the hearing threshold. On the other hand, use of short ramps may reduce timing-related inaccuracies, firstly, because short ramps yield transient brain responses which have more clearly defined morphology, and, secondly, through the use of reference information. One reason for the use of reference information is that the combined time interval between sound onset and the transient brain varies also using steady state (short onset) stimuli due to factors like inter-individual differences, alertness of the subject, and the frequency of stimulation. Therefore also with ramped stimuli the combined time interval between sound onset and the transient brain depends not only on the hearing threshold but also on other factors. Using a steady state reference stimulus with an intensity clearly exceeding the hearing threshold, the contribution of the factors such as inter-individual differences and stimulus frequency on the combined time interval can be estimated. Then this reference information can be used to obtain a more accurate estimate of the hearing threshold with the ramped stimuli.

The reference information can be obtained, for example, by recording the brain responses for the same frequency stimuli as the ramped stimuli but with short onsets. Such an acoustic reference stimulus may be, for example, a sound used separately for obtaining the reference information for the transient response. Alternatively, it can be incorporated to a stimulus which has the ramp section used for determination of hearing threshold but which also has separate portion that elicits a separate transient response which is used to obtain the reference information. Furthermore, variables such as the alertness of the test subject can be maintained the same to those that are present with the ramped stimuli by presenting the acoustic reference stimuli randomly within the same sequence as the ramped stimuli. The reference information may also be obtained from an offset response elicited by the ending of acoustic stimuli.

BRIEF DESCRIPTION OF THE DRAWINGS

In the following the invention will be described in greater detail by means of specific embodiments with reference to the attached drawings, in which.

DETAILED DESCRIPTION OF SPECIFIC EMBODIMENTS

Specific embodiments of the invention will be described. Most of the description is based on the assumption that the measured brain response is EEG response. An MEG response could be measured equally well, but MEG equipment is more expensive than EEG equipment.

Figure 1:
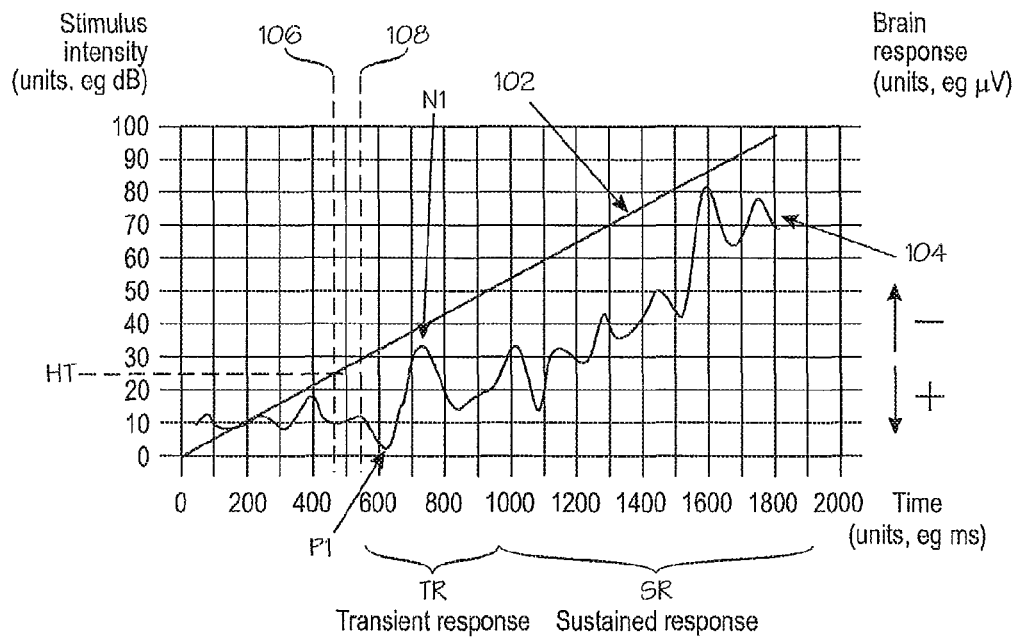
FIG. 1 shows some key concepts relating to the invention.

FIG. 1 shows some key concepts relating to the invention. Reference numeral 102 denotes an acoustic stimulus. Considering the logarithmic nature of human hearing, a preferred form of the acoustic stimulus 102 contains a rising ramp in which the slope expressed in decibels per unit of time is constant or at least approximately constant. Alternatively, the ramp could be created in another suitable domains applying compression functions such as cubic root which approximates hearing even better than logarithmic function. Reference numeral 104 denotes the test subject's brain response, which in this particular example is an EEG response. It is customary to present EEG graphs such that positive voltage fluctuations are towards the bottom of the graph and negative ones towards the top of the graph. Accordingly, expressions like "a sudden increase in the graph" actually mean a sudden decrease in measured EEG potential.

Note that the brain response 104 does not show a single EEG response but a combination, such as an average, of multiple EEG responses which are time-aligned in relation to the acoustic stimulus. The reason for combining multiple EEG responses is that human brains perform a multitude of processes simultaneously, which is why any single EEG graph is a superposition of a multitude of incoherent EEG waves. Combining (eg summing, averaging, multiplying or correlating, etc.) multiple responses which are time-aligned in respect of to the acoustic stimulus emphasizes the relative proportion of EEG signals caused by the acoustic stimulus and suppresses EEG waves caused by simultaneous processes unrelated to the acoustic stimulus.

Reference sign HT denotes the test subject's hearing threshold. Reference numeral 106 denotes the point of time at which the acoustic stimulus 102 exceeds the hearing threshold HT. Reference numeral 108 denotes the beginning of a transient response in the brain response 104.

The beginning of the transient response 108 follows the stimulus after a certain latency delay. Although the length of the latency delay depends on the exact definitions of "stimulus" and "response", the inventors have found out that its variation among humans is surprisingly small, and for most practical purposes the latency period can be treated as a constant for a specific type of stimulus. The definition of latency depends on which part of the EEG brain response is actually used for detecting the transient response. If the beginning of the latency period is defined as the time when the stimulus intensity exceeds the test subject's hearing threshold HT and its end is defined as the beginning of a detected N1 wave, the latency is typically between 100 and 150 ms. On the other hand, if the transient response is detected via the P2 wave, the latency is somewhat longer. But even if the absolute value of the latency depends on its definition, its variation among humans is not large enough to introduce any significant error to hearing threshold measurements, provided that the acoustic stimulus is dimensioned suitably.

In studies of EEG responses to acoustic stimuli, the transient response TR normally comprises a P1 wave shape followed by N1 wave shape. These may be followed by P2 or P3 wave shape. The Pn, Nn wave shapes, in turn, are defined as the $n^{th}$ positive or negative peak, respectively, after the transient stimulus. Those skilled in the art understand that the $n^{th}$ positive or negative peak do not mean noise peaks but peaks reflecting various phases in the auditory process. If the stimulus duration is long enough, the transient response is followed by a sustained response SR, which may have exhibit transient characteristics if the stimulus intensity varies. In infants, children or in some other special group of test subjects, transient brain responses may differ from those of normal adults, but any identifiable transient brain response can be used in the presently described hearing threshold determination method.

Prior art techniques for determining hearing threshold by EEG (or MEG) measurements have involved step stimuli which have been repeated at varying intensities, until an intensity was found at which the test subject's EEG/MEG response contained a recognizable P1-N1-N2-P2/P3 response. Previously, it was believed that ramp stimuli do not evoke detectable EEG responses. For instance, the previously-cited US patent application of John states, in connection with FIG. 5, that averaged EEG data essentially consists of "EEG noise", to the extent that no meaningful response is detectable in the amplitude-time domain, which is why John proposes processing sustained EEG responses in frequency-time domain. Furthermore, John does not use a continuous ramp but a rising ramp which is on-off modulated.

Thus the present invention is partially based on the surprising discovery that it is possible to obtain a meaningful EEG response from a smoothly rising ramp stimulus which begins below the hearing threshold and ends above it and has a duration of over 500 ms. That is, it was previously believed that only abrupt changes in sound properties elicit transient responses. But it is not sufficient to merely overcome the prejudice against ramp stimuli. In addition, the stimulus must fulfil certain criteria and the response must be processed appropriately for the transient response to be detectable in a manner which is repeatable and reliable for acoustic measurements. Thus the invention is also partially based on the use of special techniques on data that seemingly does not contain any transient response. The detection of this response may require techniques which go beyond time-aligned averaging of stimuli, as described elsewhere in this document. Also, the slope of the rising ramp must be neither too gentle nor too steep. If the slope is too gentle (the stimulus intensity increases too slowly), definition of the time window becomes too vague. On the other hand, if the slope is too steep (the stimulus intensity increases too quickly), any fluctuation in time causes too much fluctuation in the determined hearing threshold. Based on numerous experiments, the inventors have found out that the acoustic stimulus should increase from certainly inaudible to certainly audible over the course of a few seconds. For example, an increase from 0 to 60 dB over the course of 3 seconds means 20 dB per second. This means that a 100 ms uncertainty regarding the timing measurements translates to an uncertainty of 2 dB regarding the hearing threshold, which is insignificant for most practical purposes.

Figure 2:
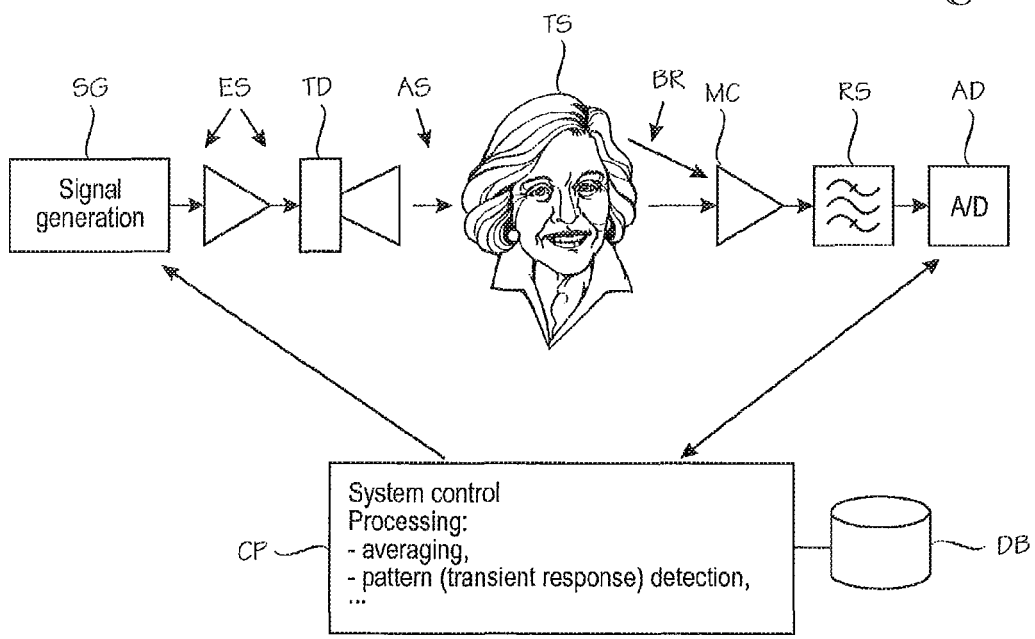
FIG. 2 shows a block diagram of a representative system architecture which can be used to implement the invention.

FIG. 2 shows a block diagram of a representative system architecture which can be used to implement the invention. A control and processing unit CP controls overall operation of the system. The control and processing unit CP, which is logically coupled to a database DB, configures a signal generation unit SG to output an electronic stimulus ES which will be converted to an acoustic stimulus AS by a transducer TD. The acoustic stimulus is applied to one or both ears of the test subject TS. A measurement circuit MC receives the test subject's brain response BR, which is digitised by an analogue-to-digital converter AD. An optional response smoother RS helps to eliminate EEG signal components which are unrelated to the relevant brain response.

The blocks of FIG. 2 described above can be more or less conventional, and a skilled reader is not expected to need detailed construction details. By way of an illustrative but non-restrictive example, the control and processing unit CP may be implemented as a microprocessor system. The signal generation unit SG may be implemented by techniques which are similar to or analogous with those used in sound chips of microcomputers. The trans-ducer TD may be implemented as a loudspeaker or earphone/headphone, for example. The measurement circuit MC comprises an electroencephalographic (EEG) or magnetoencephalographic (MEG) recorder. The optional response smoother RS may be implemented as a low-pass or band-pass filter, which is an analogue one if placed before the analogue-to-digital converter AD, or digital if placed after the A/D converter. Or, the response smoother RS may be implemented as an algorithm performed by the control and processing unit CP.

As regards the optional response smoother RS, the inventors have determined that virtually all the signal energy in transient brain response to acoustic stimuli is less than 40 Hz in frequency, which is why low-pass filtering is beneficial. An attenuation of at least 10 dB, preferably at least 20 dB at 40 Hz is desirable. An even sharper discrimination is achieved by low-pass filtering with an attenuation of at least 20 dB at 20 Hz. At the low end of the frequency spectrum, high-pass filtering with an attenuation of at least 10 dB, preferably 20 dB at 1 Hz is desirable. An even sharper discrimination is achieved by low-pass filtering with an attenuation of at least 20 dB at 3 Hz.

A key element of the present invention is the pattern detection, which may be implemented as an algorithm performed by the control and processing unit CP or as a dedicated pattern detection unit. One of the novel aspects of the pattern detection is the use of a-priori information on representative patterns of brain response to the acoustic stimulus. Such a-priori information preferably includes characteristic wave shapes of the P1 and/or N1 brain waves, optionally complemented by shapes of the P2 and P3 brain waves. For example, such wave shapes can be detected by searching for one or more of the following, in a well-defined time window relative to the stimulus:

a global or local maximum or minimum in the response;
a distinct wave or time-frequency pattern;
a continuous increase in the response in excess of a minimum threshold;
an increase in the response in excess of a minimum threshold over a period of time which does not exceed a given maximum value;
a continuous increase in the response in excess of a minimum threshold, followed by a continuous decrease in excess of a minimum threshold.

Figure 3:
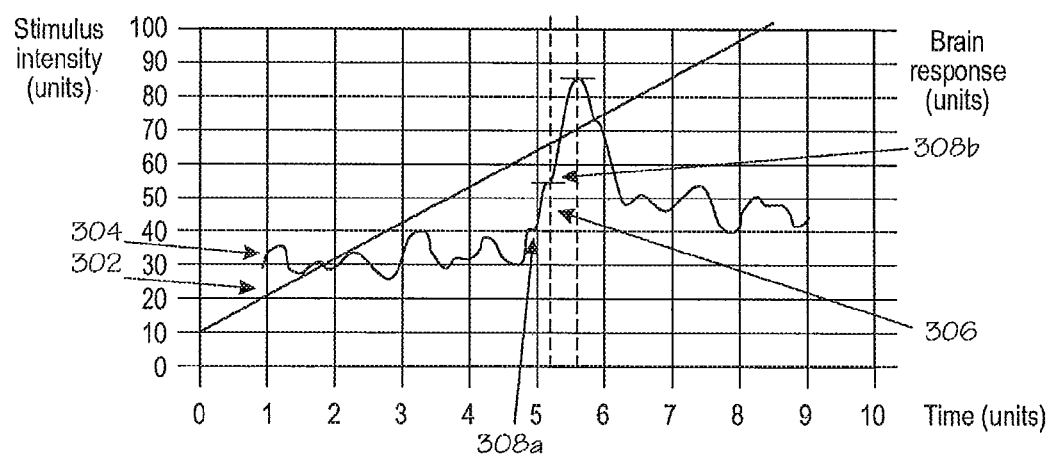
FIG. 3 shows a brain response together with a stimulus.
Figure 4:
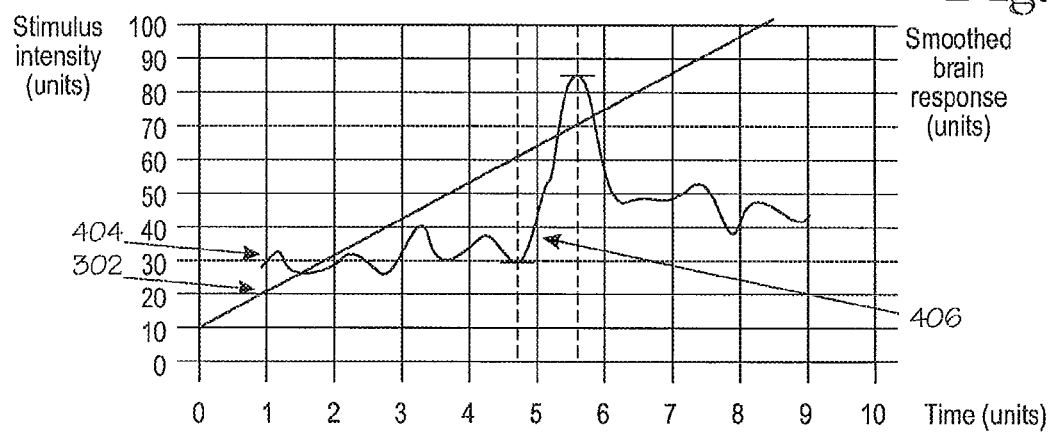
FIG. 4 shows a smoothed version of the brain response shown in FIG. 3.

A comparison of FIGS. 3 and 4 shows how the inventive technique may detect one or more predetermined patterns in a test subject's brain response, by using pre-stored a-priori information on representative patterns of brain response to an acoustic stimulus.

FIG. 3 shows a brain response together with a stimulus. Reference numeral 302 denotes an acoustic stimulus which is or contains a rising ramp. Stimulus intensity is typically expressed in logarithmic units, in which case the rising ramp is typically linear. This is only an illustrative but non-restrictive example, however. Reference numeral 304 denotes the test subject's brain response after averaging but without any smoothing or filtering. This example is based on the assumption that the pattern detection unit PD (see FIG. 1) searches for a pattern which is defined as "a continually increasing section of at least 30 units". Reference numeral 306 points to a generally increasing section of approximately 55 units in the brain response 204. But the generally increasing section 306 contains two decreasing regions 308a and 308b, which is why a pattern of "continually increasing section of at least 30 units" only begins at 5.6 units of time.

FIG. 4 shows the brain response shown in FIG. 3, after smoothing by the response smoother RS. In this example the brain response, denoted by reference numeral 304, has been smoothed by low-pass filtering. As a result of the smoothing, the increasing section 406 is free from decreasing regions (shown as items 308a and 308b in FIG. 3), and the predetermined pattern of "a continually increasing section of at least 30 units" now begins at time 4.7 units of time.

The test subject's hearing threshold can be determined as follows. As shown in FIG. 4, a pattern 406 which is representative of a beginning of hearing the acoustic stimulus is detected at time 4.7 units. At the same time, the intensity of the acoustic stimulus was approximately 62 units which, in a simple implementation, may be returned as the test subject's hearing threshold.

In a more complex implementation, particularly if the slope of the intensity of the acoustic stimulus is steep, an experimentally-determined latency may be deducted from the time at which the wave pattern 406 begins. The wave pattern 406 indicates that the test subject begins to hear the stimulus and, in the example of FIG. 4, begins at 4.7 units of time. By applying a latency of 0.3 units of time, the pattern detection unit PD can determine that the test subject can hear a stimulus at an intensity which existed at 4.7−0.3=4.4 units of time. This intensity is approximately 56 units.

A preferred value range for the latency period from the mean time point of the peak amplitude of the largest amplitude transient response is 50 to 350 ms, including all other identifiable signal sections that can be referenced to this transient response within appropriate time intervals.

It is readily apparent to a person skilled in the art that, as the technology advances, the inventive concept can be implemented in various ways. The invention and its embodiments are not limited to the examples described above but may vary within the scope of the claims.

The invention claimed is:

1. A computer-controlled method of determining a hearing threshold of a test subject, the method comprising:
    storing a-priori information on a reference transient brain response to an acoustic stimulus, the a-priori information including a wave shape of a brainwave contained in the reference transient brain response to the acoustic stimulus;
    controlling an application of the acoustic stimulus to an ear of the test subject, wherein the acoustic stimulus contains a ramp section in which a parameter of the acoustic stimulus is varied according to a ramping function having a predetermined dependency on time such that the ramp section of the acoustic stimulus transgresses the hearing threshold to be determined;
    recording an actual transient brain response of the test subject within a predetermined time window in relation to the ramp section of the acoustic stimulus that transgresses the hearing threshold to be determined;
    determining a time interval between the acoustic stimulus and the actual transient brain response based on the actual transient brain response and the a-priori information that includes the wave shape of the brainwave contained in the reference transient brain response; and
    determining the hearing threshold of the test subject based on the predetermined dependency on time of the ramping function and based on the time interval determined based on the actual transient brain response and the a-priori information that includes the wave shape of the brainwave contained in the reference transient brain response, the determining of the hearing threshold being performed by a processor.

2. The method according to claim 1, wherein the determining of the time interval between the acoustic stimulus and the actual transient brain response comprises processing a plurality of recorded brain responses in a combinatory process that combines the recorded brain responses.

3. The method according to claim 2, wherein the combinatory process comprises time-aligning the plurality of recorded brain responses in relation to the acoustic stimulus and at least one of summing, averaging, or multiplying the time aligned plurality of recorded brain responses.

4. The method according to claim 1, wherein the determining of the time interval between the acoustic stimulus and the actual transient brain response comprises:
    deriving temporal information on the actual transient brain response in a recorded brain response; and
    determining the time interval between the acoustic stimulus and the actual transient brain response based on the derived temporal information.

5. The method according to claim 1, further comprising determining a latency period of the reference transient brain response; and wherein the determining of the hearing threshold is based on the determined latency period of the reference transient brain response.

6. The method according to claim 1, further comprising compensating for a variation in the time interval between the acoustic stimulus and the actual transient brain response, where the variation is caused by factors other than the hearing threshold of the test subject, by using the a-priori information that includes the wave shape of the brainwave contained in the reference transient brain response.

7. The method according to claim 6, further comprising obtaining the wave shape of the brainwave contained in the reference transient brain response by presenting an acoustic reference stimulus to the test subject, wherein the acoustic reference stimulus is temporally separate from the ramp section of the acoustic stimulus and elicits a response temporally separate from the actual transient brain response.

8. The method according to claim 1, wherein the ramp section has a duration of 100 ms to 5 s.

9. The method according to claim 1, wherein the recording of the actual transient brain response includes low-pass filtering a plurality of recorded brain responses with an attenuation of at least 10 decibels at 40 Hz.

10. The method according to claim 1, wherein the recording of the actual transient brain response includes high-pass filtering a plurality of recorded brain responses with an attenuation of at least 10 dB at 1 Hz.

11. The method according to claim 1, wherein the predetermined time window in relation to the ramp section spans a duration of the ramp section plus at least 200 ms.

12. A computer system to determine a hearing threshold of a test subject, the computer system comprising:
    memory means for storing a-priori information on a reference transient brain response to an acoustic stimulus, the a-priori information including a wave shape of the brainwave contained in the reference transient brain response to the acoustic stimulus:
    first interface means for controlling an application of the acoustic stimulus to an ear of the test subject, wherein the acoustic stimulus contains a ramp section in which a parameter of the acoustic stimulus is varied according to a ramping function having a predetermined dependency on time such that the ramp section of the acoustic stimulus transgresses the hearing threshold to be determined;
    second interface means for recording an actual transient brain response of the test subject within a predetermined time window in relation to the ramp section of the acoustic stimulus that transgresses the hearing threshold to be determined;

first logic means for determining a time interval between the acoustic stimulus and the actual transient brain response based on the actual transient brain response and the a-priori information that includes the wave shape of the brainwave contained in the reference transient brain response; and second logic means for determining the hearing threshold of the test subject based on the predetermined dependency on time of the ramping function and based on the time interval determined based on the actual transient brain response and the a-priori information that includes the wave shape of the brainwave contained in the reference transient brain response.

13. A non-transitory software product for a computer, wherein execution of the software product in the computer causes the computer to perform operations comprising:

storing a-priori information on a reference transient brain response to an acoustic stimulus, the a-priori information including, a wave shape of a brainwave contained in the reference transient brain response to the acoustic stimulus;

controlling an application of the acoustic stimulus to an ear of the test subject, wherein the acoustic stimulus contains a ramp section in which a parameter of the acoustic stimulus is varied according to a ramping function having a predetermined dependency on time such that the ramp section of the acoustic stimulus transgresses the hearing threshold to be determined;

recording an actual transient brain response of the test subject within a predetermined time window in relation to the ramp section of the acoustic stimulus that transgresses the hearing threshold to be determined:

determining a time interval between the acoustic stimulus and the actual transient brain response based on the actual transient brain response and the a-priori information that includes the wave shape of the brainwave contained in the reference transient brain response; and determining the hearing threshold of the test subject based on the predetermined dependency on time of the ramping function and based on the time interval determined based on the actual transient brain response and the a-priori information that includes the wave shape of the brainwave contained in the reference transient brain response.

* * * * *